| United States Patent [19] | | [11] | 4,018,897 |
|---|---|---|---|
| Molloy | | [45] | Apr. 19, 1977 |

[54] ANTIARRHYTHMIC AGENTS

[75] Inventor: Bryan B. Molloy, Indianapolis, Ind.

[73] Assignee: Eli Lilly and Company, Indianapolis, Ind.

[22] Filed: Mar. 15, 1976

[21] Appl. No.: 667,224

Related U.S. Application Data

[62] Division of Ser. No. 485,488, July 3, 1974, Pat. No. 3,972,935.

[52] U.S. Cl. .............................. 424/330; 424/248.4; 424/248.58; 424/267; 424/274; 424/316; 424/329

[51] Int. Cl.$^2$ ....................................... A61K 31/135

[58] Field of Search .................................... 424/330

[56] References Cited

UNITED STATES PATENTS

| 3,255,249 | 6/1966 | Howe et al. ................ 260/570.6 X |
|---|---|---|
| 3,281,468 | 10/1966 | Mills ............................... 260/570.6 |
| 3,312,733 | 4/1967 | Howe ............................ 260/501.17 |
| 3,923,813 | 12/1975 | Vanhoof et al. .................... 424/330 |
| 3,923,815 | 12/1975 | Vanhoof et al. .................... 424/330 |
| 3,923,887 | 12/1975 | Vanhoof et al. .................... 424/330 |
| 3,981,872 | 9/1976 | Vanhoof et al. ............. 260/247.2 A |
| 3,984,464 | 10/1976 | Vanhoof et al. .............. 260/501.18 |

*Primary Examiner*—Norman A. Drezin
*Attorney, Agent, or Firm*—Charles W. Ashbrook; Everet F. Smith

[57] ABSTRACT

Novel 1-aryl-1-benzocycloalkyl-4-aminobutanes and 1-aryl-1-benzocycloalkyl-4-amino-1-butenes are useful as antiarrhythmic agents.

4 Claims, No Drawings

ANTIARRHYTHMIC AGENTS

This is a division of application Ser. No. 485,488, filed July 3, 1974.

BACKGROUND OF THE INVENTION

This invention relates to certain butylamines and butenylamines. In particular, this invention relates to certain butyl and butenylamines having aryl and benzocycloalkyl disubstitution in the 4-position. The novel compounds provided herein are valuable pharmacological agents, especially useful in the treatment of cardiac arrhythmias in humans.

There are several types of arrhythmias which afflict mankind, and each type may have a different underlying condition as its cause. The more serious conditions causing arrhythmias are generally myocardial infarction and digitalis toxicity. When treating arrhythmias, it is important to understand the pharmacologic action of the drug being used, and it is important to remember that the pharmacologic action of the drug selected may vary, depending on the state of the myocardium. Several drugs are available for treating cardiac arrhythmias. Quinidine is a drug that depresses myocardial contractility and decreases the rate of conduction in the myocardium. It is used mainly to prevent tachyarrhythmias; however, several undesirable side effects normally accompany its use. Procainamide has practically the same pharmacological actions as quinidine, with about the same effect on arrhythmias; however procainamide is safer than quinidine for intravenous use. Lidocaine is considered one of the most effective antiarrhythmic agents and is used primarily to combat ventricular tachyarrhythmias. It is especially useful in patients with recent myocardial infarction. Lidocaine doesn't cause a drop in blood pressure as does quinidine and procainamide; however, lidocaine does display toxic effects on the central nervous system, evidenced by symptoms such as drowsiness, twitchings and convulsions.

Research scientists are constantly looking for new antiarrhythmic agents because of the severity of these diseases of the heart, and because of the serious side effects commonly encountered with the use of currently available drugs. Several indanyl derivatives have recently been prepared which have displayed varying degrees of antiarrhythmic activity. For example, very potent antiarrhythmic agents, which are N,N-dialkyl-N'-(2-indanyl)-N'-phenyl alkylene diamines, are described in Canadian Pat. No. 910907.

The compounds of this invention are butylamine and butenylamine derivatives which display antiarrhythmic activity. It is an object of this invention to provide novel compounds which are useful in treating cardiac arrhythmias.

SUMMARY OF THE INVENTION

The compounds of this invention have the formula

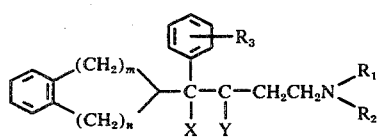

in which $m$ is 0, 1, or 2; $n$ is 0, 1, or 2, $m+n$ is 2 or 3; $R_1$ and $R_2$ independently are hydrogen, $C_1$-$C_4$ alkyl, or a lower alkenyl group having the formula $CH_2R_4$, in which $R_4$ is $C_2$-$C_5$ alkenyl, or $R_1$ and $R_2$ together with the adjacent nitrogen atom form a heterocyclic ring system; $R_3$ is hydrogen, methyl, methoxy, trifluoromethyl, or halogen. X and Y are both hydrogen, or taken together X and Y form a double bond. The pharmaceutically acceptable acid addition salts are included within the scope of the invention. Also included herein are the pharmaceutically acceptable quaternary ammonium salts of the tertiary amines of this invention.

The novel compounds provided by the present invention are prepared by treating a readily available 1-aryl-1-benzocycloalkyl-1-butene, which butene bears in the 4-position a displaceable group such as a chlorine or bromine atom for instance, with an amine to provide the desired 1-aryl-1-benzocycloalkyl-4-amino-1-butenes of the invention. Reduction of the butenes thus formed leads to the corresponding aminobutanes of the invention.

The compounds of this invention are useful in converting heart arrhythmias to a normal rhythm.

DETAILED DESCRIPTION OF THE INVENTION

As hereinbefore indicated, the compounds of this invention have the formula

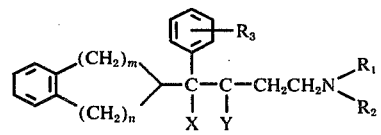

$R_1$ and $R_2$ in the above formula are the same or are different and are selected from among hydrogen, $C_1$-$C_4$ alkyl, or $CH_2R_4$, wherein $R_4$ is $C_2$-$C_5$ alkenyl, or $R_1$ and $R_2$ together with the adjacent nitrogen atom form a ring system selected from among pyrrolidino, piperidone, or morpholino.

Examples of $C_1$-$C_4$ alkyl groups include both straight and branched chain lower alkyl groups such as methyl, ethyl, n-propyl, isopropyl, n-butyl, isobutyl, and like groups.

$R_1$ and $R_2$ also can be alkenyl groups of the formula $CH_2R_4$, examples of which include 2-propenyl, 2-butenyl, 3-butenyl, 3-methyl-2-butenyl, 3-methyl-3-pentenyl, 4-hexenyl, 5-hexenyl, and the like. $R_3$ in the above formula is a phenyl substituent selected from among hydrogen, methyl, methoxy, trifluoromethyl and halogen. The term "halogen" as used herein refers to fluorine, chlorine, bromine, and iodine. The preferred compounds of the invention are those wherein $R_3$ is hydrogen.

X and Y are both hydrogen, or taken together, X and Y form a double bond.

The aminobutenes and the aminobutanes of this invention are disubstituted in the 4-position with a phenyl group and with a benzocycloalkyl group. As indicated in the above formula, the benzocycloalkyl group can be an indanyl group or a tetrahydronaphthyl group. For example, when $m$ is 0 and $n$ is 2, the substituent is a 1-indanyl group, and when $m$ is 1 and $n$ is 1, the substituent is a 2-indanyl group. Similarly, when $m$ is 0 and $n$ is 3, the substituent is a 1-(1,2,3,4-tetrahydronaphthyl) group, and when $m$ is 1 and $n$ is 2, the substituent is a 2-(1,2,3,4-tetrahydronaphthyl) group.

The pharmaceutically acceptable acid addition salts of the amines are included within the scope of this invention. Pharmaceutically acceptable salts of amines are well known to those in the art, and it is generally recognized that the particular salt formed is not critical. The salt formed, however, must be pharmaceutically acceptable and substantially non-toxic to animal organisms. Typical acid addition salts are those prepared with the mineral acids, especially those prepared with acids such as hydrochloric, hydrobromic, sulfuric, nitric, phosphoric, and like acids. Organic acids such as formic, acetic, butyric, citric, maleic, succinic, oxalic, benzoic, methanesulfonic, p-toluenesulfonic, and the like, can also be used to form acceptable salts.

Pharmaceutically acceptable quaternary ammonium salts are also included herein and are important pharmacological agents. The particular salt formed is not critical, but the salt must be substantially non-toxic to animal organisms. Any of a number of anions can be associated with quaternary salts, and these are well known to chemists and biologists. Preferred quaternary ammonium salts are those prepared with $C_1$-$C_4$ lower alkyl alkylating agents. Generally, these salts are prepared by treating the amine with alkylating agents such as alkyl halides, alkylsulfates, arylsulfonates, and the like. Typical alkylating agents include methyl iodide, ethyl bromide, n-propyl chloride, dimethyl sulfate, isopropyl bromide, isobutyl iodide, and the like. Other acceptable salts are prepared with $CH_2R_4$ alkylating agents, wherein $R_4$ is as defined hereinabove. Examples of these alkylating agents include allyl bromide, 3-butenyl iodide, 3-pentenyl chloride, 4-pentenyl chloride, 5-hexenyl iodide, and the like. When the anion of a quaternary ammonium salt is a halide ion, these anions can be replaced by other anions if desired, for example by metathesis. An anion such as sulfate, sulfonate, nitrate, hydroxide, perchlorate, tetrafluoroborate, acetate, butyrate, and the like, can be incorporated into the ammonium salt if desired.

Illustrative examples of compounds provided by the present invention are as follows:

1-Phenyl-1-(2-indanyl)-4-aminobutane;
1-Phenyl-1-(2-indanyl)-4-methylamino-1-butene;
1-Phenyl-1-(2-indanyl)-4-isobutylaminobutane;
1-(4-Trifluoromethylphenyl)-1-(2-indany;l)-4-allylamino-1-butene;
1-(3-Chlorophenyl)-1-(2-indanyl)-4-amino-1-butene;
1-(2-Methylphenyl)-1-(2-indanyl)-4-methylaminobutane;
1-Phenyl-1-(2-indanyl)-4-amino-1-butene hydrobromide;
1-Phenyl-1-(2-indanyl)-4-aminobutane hydroacetate;
1-Phenyl-1-(1-indanyl)-4-n-propylaminobutane hydroiodide;
1-Phenyl-1-(2-indanyl)-4-n-butylamino-1-butene hydrogen nitrate;
1-Phenyl-1-(2-indanyl)-4-(5-hexenylamino)butane hydrogen maleate;
1-Phenyl-1-(2-indanyl)-4-diethylaminobutane;
1-Phenyl-1-(2-indanyl)-4-diisopropylaminobutane;
1-(3-chlorophenyl)-1-(1-indanyl)-4-dimethylaminobutane;
1-(4-methylphenyl)-1-(2-indanyl)-4di-n-propyl-l-butene;
1-Phenyl-1-(2-indanyl)-4-diethylamino-1-butene;
1-(3-methoxyphenyl)-1-(2-indanyl)-4-n-butylmethylamino-1-butene;
1-Phenyl-1-(2-indanyl)-4-piperidinobutane;
1-Phenyl-1-(2-indanyl)-4-morpholinobutane;
1-Phenyl-1-(2-indanyl)-4-pyrrolidinobutane;
1-(4-Trifluoromethylphenyl)-1-(2-indanyl)-4-diethylaminobutane hydrochloride;
[4-Phenyl-4-(2-indanyl)butyl]triethylammonium iodide;
[4-Phenyl-4-(2-indanyl)butyl]diethylmethylammonium methanesulfate;
[4-Phenyl-4-(1-indanyl)-3-butenyl]allyldiethylammonium bromide;
[4-Phenyl-4-(2-indanyl)-3-butenyl]trimethylammonium hydroxide.
1-Phenyl-1-[1-(1,2,3,4-tetrahydronaphthyl)]-4-di-isopropylaminobutane;
1-Phenyl-1-[2-(1,2,3,4-tetrahydronaphthyl)]-4-isopropylmethylaminobutane;
1-(2-Bromophenyl)-1-[-(1,2,3,4-tetrahydronaphthyl)]-4-diethylaminobutane hydroacetate;
1-(3-Iodophenyl)-1-[2-(1,2,3,4-tetrahydronaphthyl)]-4-aminobutane hydrobromide;
1-(3-Methylphenyl)-1-[2-(1,2,3,4-tetrahydronaphthyl)]-4-piperadinobutane methiodide;
1-(4-Trifluoromethylphenyl)-1-[1-(1,2,3,4-tetrahydronaphthyl)]-4-allylmethylamino-1-butene;
1-Phenyl-1-[2-(1,2,3,4-tetrahydronaphthyl)]-4-di-isopropylaminobutane hydroiodide;
1-(4-Iodophenyl)-1-[1-(1,2,3,4-tetrahydronaphthyl)]-4-di-n-butylamino-1-butene;
1-(2-Methylphenyl)-1-[2-(1,2,3,4-tetrahydronaphthyl)]-4-di-allylamino-1-butene hydrochloride;
1-(4-Methoxyphenyl)-1-[2-(1,2,3,4-tetrahydronaphthyl)]-4-ethylaminobutane;
1-(3-Methoxyphenyl)-1-[2-(1,2,3,4-tetrahydronaphthyl)]-4-diethylaminobutane hydrochloride;
1-(2-Methoxyphenyl)-1-[2-(1,2,3,4-tetrahydronaphthyl)]-4-morpholinobutane;
[4-Phenyl-4-[2-(1,2,3,4-tetrahydronaphthyl)]butyl]-trimethylammonium methanesulfate In accordance with the invention, the butenyl compounds are prepared by reacting an amine with a suitably substituted butene bearing a readily displaceable group. More specifically, a 1-aryl-1-benzocycloalkyl-1-butene, with a displaceable group in the 4-position, is treated with an amine, thereby providing the aminobutenes of this invention. Some examples of amines useful in preparing compounds disclosed herein include ammonia, methylamine, ethylamine, isopropylamine, n-butylamine, allylamine, 4-hexenylamine, dimethylamine, diethylamine, diisopropylamine, diallylamine, methylethylamine, methylallylamine, ethyl(2-methyl-3-butenyl)amine, trimethylamine, triethylamine, tri-n-propylamine, triallylamine, tri-3-hexenylamine, piperadine, pyrrolidine, morpholine, and the like. Preferred butene starting materials are those wherein the displaceable group is a halogen atom, especially chlorine, bromine, or iodide. Typical butenes useful in preparing the compounds of the invention include 1-phenyl-1-(2-indanyl)-4-chloro-1-butene, 1-(3-methoxyphenyl)-1-(1-indanyl)-4-bromo-1-butene, 1-(4-chlorophenyl)-1-[1-(1,2,3,4-tetrahydronaphthyl)]-4-iodo-1-butene, 1-phenyl-1-[2-(1,2,3,4-tetrahydronaphthyl)]-4-chloro-1-butene, and the like. The amine and the suitably substituted butene are normally commingled in approximately equimolar quantities, although an excess of either reactant can be employed if desired. The reaction is best carried out in an unreactive organic solvent. A suitably solvent can be selected from among any of a number of unreactive organic solvents, including alcohols such as methanol, ethanol, isopropanol; chlorinated hydrocarbons such as chloroform or dichloromethane; aromatic solvents such as benzene, toluene, or xylene; ethers such as diethyl ether, 1,2-dimethoxyethane or dioxane, and the like. Mixtures of solvents can be used if desired, for example a mixture of ethanol and benzene or ethanol and water. A preferred reaction solvent is ethyl alcohol, or alternatively a mixture of ethyl alcohol and benzene. The reaction is substantially complete after about 10 to 20 hours when carried out at a temperature below about 150° C. Generally, the temperature is maintained in the range of about 50° to 100° C. The product is a primary, secondary, or tertiary amine, or a quaternary ammonium salt, depending upon the particular aminating agent used in the reaction. When the aminating agent is a tertiary amine for example, the product is the corresponding quaternary ammonium salt. Generally, the quaternary ammonium salts are highly crystalline solids and can be filtered from the reaction mixture and further purified if desired, for example by recrystallization. When the product is a primary, secondary or tertiary amine, such product can be isolated either as the free amine or as an acid addition salt by suitable adjustment of the pH. For example, the reaction mixture can be evaporated to dryness and the residue redissolved in water. The pH of the aqueous solution can be adjusted to about 8 to 10 by the addition of a suitable base, such as aqueous sodium hydroxide for example. The basic solution is then extracted with a suitable water immiscible organic solvent, such as ethyl acetate or diethyl ether for instance, and the organic solution can then be evaporated to give the product in the form of the free amine. The free amine can be further purified if desired by standard methods such as distillation, chromatography, crystallization, or the like. Alternatively, the free amine can be isolated as an acid addition salt by treating the amine with a suitable acid, especially a mineral acid such as hydrochloric or hydrobromic acid for example, in a mutual solvent such as ethyl acetate or diethyl ether, thereby precipitating the corresponding acid addition salt. Generally, the amine acid addition salts are highly crystalline solids and can be filtered and further purified if desired by recrystallization from solvents such as ethanol, ethyl acetate, water, or the like. When desired, the acid addition salts can be converted back to the free amine by basification, for example by the addition of an appropriate base such as sodium hydroxide or sodium bicarbonate.

The preferred aminobutenes of the invention are those wherein the amine is a tertiary amine, such as a dialkylaminobutene for instance. These tertiary amines can be converted to quaternary ammonium salts by normal procedures that are discussed in detail hereinbelow. Additionally, the primary and secondary aminobutenes can be converted to secondary, tertiary and quaternary compounds by general alkylation procedures that are discussed hereinbelow. The aminobutenes of this invention exist as cis and trans isomers, as well as mixtures thereof. It will be understood that the separated isomers, as well as the mixtures of geometrical isomers, are included within the scope of this invention.

In a further embodiment of the invention, the aminobutenes prepared as described hereinabove are reduced to provide the aminobutanes of the invention. More specifically, the aminobutenes can be reduced by hydrogenation wherein the aminobutene is dissolved in an inert solvent and hydrogenated with hydrogen in the presence of a suitable hydrogenation catalyst. Suitable inert solvents include alcohols such as methanol or ethanol; esters such as methyl acetate or ethyl acetate; or ethers such as diethyl ether or tetrahydrofuran. The particular solvent selected for the reaction is not critical, but preferably the solvent used is one in which the aminobutene is at least partially soluble. Suitable hydrogenation catalysts include certain noble metals such as platinum, palladium, or rhodium, as well as active grades of Raney nickel. The noble metal catalysts may be employed as finely divided metals, such as that obtained by the hydrogenation of platinum oxide in the hydrogenation apparatus for example. Alternatively, the metal catalysts can be employed as deposited on the surface of an inert support such as carbon, alumina, barium sulfate, calcium carbonate, or the like. A preferred hydrogenation catalyst, for example, is palladium on carbon. The reduction reaction is generally carried out at a temperature below about 100° C., preferably at a temperature in the range of about 0° to 50° C. The hydrogen gas pressure is normally maintained in the range of about 30 to 2000 p.s.i., preferably at about 50 to 100 p.s.i., and the reaction is substantially complete after about 2 to 20 hours. The aminobutanes thus prepared can be recovered by removal of the hydrogenation catalyst, for example by filtration, and evaporation of the solvent to provide the free amine. Further purification can be accomplished, if desired, by normal procedures such as distillation or chromatography. The acid addition salts are readily obtained by reaction of the aminobutane with the appropriate acid, as described hereinabove for the aminobutenes.

An alternative method of preparation of the aminobutanes of the invention comprises catalytic reduction of 1-aryl-1-benzocycloalkyl-4-halo-1-butenes to provide the corresponding halobutanes, which can then be aminated with an appropriate amine to provide the desired 1-aryl-1-benzocycloalkyl-4-aminobutanes.

It is to be understood that reduction of a butene provides a butane which possess an asymmetric center and thus exists as $d$ and $l$ stereoisomers. Both the $d$ and the $l$ isomer, as well as the $dl$ mixture, are included within the scope of the present invention.

As hereinbefore indicated, the aminobutenes and aminobutanes, wherein the amino group is primary, secondary, or tertiary, can be converted to pharmaceutically acceptable acid addition salts by the reaction of the appropriate acid with the free amine in a mutual solvent. Similarly, these aminobutenes and aminobutanes can be converted to quaternary ammonium salts which are valuable pharmacological agents. Generally, a tertiary amine, for example a 1-aryl-1-benzocycloalkyl-4-dialkylaminobutane, is treated with an alkylating agent in an unreactive solvent to provide the corresponding quaternary ammonium salt. Typical unreactive solvents include acetone, benzene, diethyl ether, methanol, tetrahydrofuran, or the like. Typical alkylating agents used to quaternize the amine are lower alkyl halides such as methyl chloride, ethyl iodide, allyl bromide, as well as alkyl sulfates such as methyl sulfate or ethyl sulfate. The reactants are normally employed in approximately equimolar amounts; however, an excess of either can be used if desired. The product quaternary salts are typically crystalline solids and are generally recovered by filtration. When the quaternary salt has a halogen anion, such as chloride or iodide for example, these anions can be converted to other anions when desired, as indicated hereinabove. More specifically, a quaternary ammonium halide can be reacted with aqueous silver oxide to afford silver halide and the corresponding quaternary ammonium hydroxide. The quaternary ammonium hydroxide can then be neutralized with an appropriate acid, such as methanesulfonic acid, acetic acid, butyric acid, nitric acid, p-toluenesulfonic acid, or the like, thereby providing the corresponding pharmaceutically acceptable quaternary ammonium salt.

Alkylation of aminobutenes and aminobutanes, wherein the amino group is primary or secondary, can be carried out when desired. For example, a primary aminobutane can be further alkylated with an appropriate alkylating agent to provide the corresponding secondary aminobutane, which can be alkylated still further to provide the corresponding tertiary amine. The alkylation reactions are general and are well known to those in the art.

As hereinbefore indicated, the preferred starting materials for the compounds of this invention are 1-aryl-1-benzocycloalkyl-4-halobutenes. These compounds are readily available from known starting materials. More specifically, the disubstituted halobutenes are generally prepared from benzocycloalkyl aryl ketones, which compounds are well known. In particular, a benzocycloalkyl aryl ketone, such as 2-indanyl phenyl ketone for example, is treated with a cyclopropyl Grignard reagent to provide a benzocycloalkyl aryl cyclopropyl carbinol. The cyclopropyl carbinol is treated with an acid, especially a mineral acid such as hydrochloric or hydroiodic acid for example, thereby opening the cyclopropyl ring and dehydrating the alcohol to afford the corresponding disubstituted butenyl halide.

The reaction of a benzocycloalkyl aryl ketone with a cyclopropyl Grignard reagent is preferably carried out in an unreactive organic solvent. Solvents generally used for Grignard reactions are well known to those in the art and include solvents such as diethyl ether, diglyme, 1,2-dimethoxyethane, dioxane, furan, tetrahydrofuran, and the like. The particular solvent selected is not of a critical nature. The Grignard reagent is prepared by established procedures which comprise reacting magnesium metal with the appropriate alkyl halide, in particular a cyclopropyl halide such as cyclopropyl bromide for example. The cyclopropyl magnesium halide is then reacted with the benzocycloalkyl aryl ketone, normally in an equimolar amount; however, either can be used in excess of the other if desired. Preferably, the Grignard reagent is employed in slight excess of the ketone in order to ensure more complete reaction. The reaction is generally carried out at a temperature below about 150°, the most convenient temperature being the reflux temperature of the particular solvent being used. The reaction is substantially complete within about 2 to 12 hours, although longer reaction times are generally not detrimental to the production of the product. The product, a cyclopropyl benzocycloalkyl aryl carbinol, is recovered by hydrolyzing the reaction mixture with a proton source, such as water for example, and extraction of the product into a suitable solvent, such as diethyl ether or ethyl acetate. Evaporation of the solvent affords the desired carbinol which can be used directly, or if desired, the carbinol can be further purified by standard procedures, such as distillation or chromatography for example.

The cyclopropyl benzocycloalkyl aryl carbinol is treated with a suitable acid to effect ring opening of the cyclopropyl ring system and concomitant dehydration. Preferred acids for the reaction include the mineral acids such as hydrochloric, hydrobromic, or hydroiodic acid. Acids such as methanesulfonic or p-toluenesulfonic acid can be used if desired. The reaction is generally carried out in an essentially anhydrous organic solvent; however, the particular solvent is not critical. Typical solvents generally employed include lower alkanoic acids such as formic acid, acetic acid or propionic acid; ethers such as dioxane; or amides such as N,N-dimethylformamide can also be used. The reaction is carried out at a temperature below about 70° C, preferably at a temperature in the range of about 0° to 30° C. The reaction is normally complete within about 1 hour to about 8 hours. The product, a benzocycloalkyl aryl butene, can be recovered by diluting the reaction mixture with a suitable solvent, preferably water, and extracting the butene into a water immiscible solvent such as diethyl ether or ethyl acetate. If desired, the butene can be further purified by normal procedures such as distillation, crystallization or chromatography.

The compounds of this invention are useful pharmacological agents, especially in the treatment of cardiac arrhythmias in humans. The compounds can be administered by the oral route or by the parenteral route, and in cases of severe arrhythmias, it may be desirable to administer the compounds intraveneously. Generally, a compound of this invention can be employed in combination with one or more pharmaceutically acceptable diluents or carriers. For oral administration, for example, the compound of this invention can be mixed with carriers such as starch powder, sucrose, cellulose, magnesium stearate, and the like. The dose can be formulated as a tablet or as a capsule. The normal adult oral dose will contain from about 0.005 to about 2.0 g. of active ingredient, and will be administered to a patient suffering from an arrhythmia at intervals of about 4 to 10 hours until a tolerance level has been reached, or until a conversion to a normal rhythm is maintained. The pharmaceutical preparations may contain, in addition to the active component of the present invention, one or more other pharmacologically active substances, especially other antiarrhythmic agents such as lidocaine for example.

In the case of parenteral administration, the intravenous route is preferred. A suitable pharmaceutical preparation for intravenous administration will include a compound of this invention in the amount of from about 0.1 to about 1.0 g. admixed with a suitable carrier such as 5 percent aqueous glucose or 0.9 percent saline solution for example, generally in the amount of about 50 to 100 cc. of solution. Such a solution can be administered dropwise to a patient suffering from an arrhythmia over a period of from 5 to about 60 minutes. The compounds of this invention are especially useful in patients refractory to other antiarrhythmic agents such as procainamide or quinidine for example.

The following detailed examples are added to more fully illustrate, but not to limit, the scope of the invention.

EXAMPLE 1

1-Phenyl-1-(2-indanyl)-4-diethylamino-1-butene

To a solution of 29.5 g. of 1-phenyl-1-(2-indanyl)-4-chloro-1-butene in 125 cc. of 95 percent (v/v) ethanolbenzene (commercial 2B ethanol) was added 100 cc. of diethylamine in one portion. The reaction mixture was shaken and heated in a sealed bomb to about 100° C for 16 hours. The reaction mixture was cooled to about 25° C. and the solvent was removed under reduced pressure to afford the product as an oily residue. The oil was dissolved in 400 cc. of diethyl ether and shaken with 5N sodium hydroxide and washed with water. The ethereal solution was dried and the solvent was removed under reduced pressure, affording 1-phenyl-1-(2-indanyl)-4-diethylamino-1-butene.

EXAMPLES 2–5

The following aminobutenes are prepared by the procedure of example 1, from the corresponding halobutene and amine.

1-Phenyl-1-(1-indanyl)-4-methylamino-1-butene;
1-(4-Chlorophenyl)-1-(2-indanyl)-4-amino-1-butene;
1-(4-Methylphenyl)-1-(2-indanyl)-4-allylmethalamino-1-butene;
1-Phenyl-1-[2-(1,2,3,4-tetrahydronaphthyl)]-4-ethylisopropylamino-1-butene.

EXAMPLE 6

1-Phenyl-1-(2-indanyl)-4-diethylamino-1-butene hydrogen oxalate

A solution of 693 mg. of oxalic acid in 20 cc. of ethyl acetate was added to a solution of 1-phenyl-1-(2-indanyl)-4-diethyl aminobutene in 30 cc. of ethyl acetate. The reaction mixture was allowed to stand at room temperature for 2 hours, at which time the crystalline product was filtered to provide the oxalate salt of 1-phenyl-1-(2-indanyl)-4-diethylamino-1-butene. M.P. 98°–101° C.

EXAMPLE 7

1-Phenyl-1-(2-indanyl)-4-diethylamino-1-butene hydrochloride

Dry hydrogen chloride gas was bubbled into a solution of 1-phenyl-1-(2-indanyl)-4-diethylamino-1-butene in diethyl ether. The ethereal solution was concentrated under reduced pressure to provide the product as a white solid residue which was purified by recrystallization from an ethyl acetate:ligroin solvent mixture. Crystalline 1-phenyl-1-(2-indanyl)-4-diethylamino-1-butene hydrochloride was recovered by filtration. M.P. 110°–112° C.
Analysis, Calc. for $C_{23}H_{30}NCl$ (percent): C, 77.61; H, 8.50; N, 3.99; Cl, 9.96.
Found (percent): C, 77.41; H, 8.61; N, 3.76; Cl, 10.17.

EXAMPLE 8

1-Phenyl-1-(2-indanyl)-4-diethylaminobutane

A solution of 23.5 g. of 1-phenyl-1-(2-indanyl)-4-diethylamino-1-butene in 375 cc. of 95 percent (v/v) ethanol:benzene was stirred while 1.5 g. of 5 percent palladium on carbon was added in one portion. The reaction mixture was stirred for 6 hours at 24° C. under a hydrogen gas atmosphere at 60 p.s.i. After filtering off the hydrogenation catalyst, the filtrate was concentrated to dryness under reduced pressure to provide 1-phenyl-1-(2-indanyl)-4-diethylaminobutane.

EXAMPLES 9–11

The following aminobutanes are prepared by the method of Example 8 from the corresponding aminobutenes:

1-Phenyl-1-(2-indanyl)-4-aminobutane;
1-Phenyl-1-(2-indanyl)-4-ethylaminobutane;
1-(4-Chlorophenyl)-1-[1-(1,2,3,4-tetrahydronaphthyl)]-4-diethylaminobutane.

EXAMPLE 12

1-Phenyl-1-(2-indanyl)-4-diethylaminobutane hydrochloride

To a solution of 1-phenyl-1-(2-indanyl)-4-diethylaminobutane in diethyl ether was added anhydrous hydrogen chloride gas. The reaction mixture stood at room temperature for 20 minutes, and the solvent was then removed under reduced pressure, leaving the product as a solid residue. The product was recrystallized from ethyl acetate, affording 1-phenyl-1-(2-indanyl)-4-diethylaminobutane hydrochloride. M.P. 132°–34° C.
Analysis, Calc. for $C_{23}H_{32}NCl$ (percent): C, 77.17; H, 9.01; N, 3.91; Cl, 9.90.
Found (percent): C, 77.09; H, 8.98; N, 3.81; Cl, 9.99.

EXAMPLE 13

4-Phenyl-4-(2-indanyl)-butyldiethylmethylammonium methanesulfate

To a stirred solution of 3.14 g. of 1-phenyl-1-(2-indanyl)-4-diethylaminobutane in 50 cc. of benzene was added 1.26 g. of dimethyl sulfate. The reaction mixture was stirred at room temperature for 12 hours. The crystalline product was filtered off and recrystallized from ethyl acetate and methanol, providing 3.85 g. of 4-phenyl-4-(2-indanyl)-butyldiethylmethylammonium methanesulfate. M.P. 118°–121° C.
Analysis, Calc. for $C_{25}H_{37}NO_4S$ (percent): C, 67.08; H, 8.33; N, 3.13; S, 7.16.
Found (percent): C, 67.37; H, 8.11; N, 3.17; S, 7.01.

EXAMPLE 14

1-Phenyl-1-(2-indanyl)-4-methyl-n-propylaminobutane

A solution of 1-phenyl-1-(2-indanyl)-4-bromobutane in ethanol was stirred at room temperature while methylpropylamine was added. The reaction mixture was stirred several hours at about 100° C. After cooling the reaction mixture to room temperature, the solvent was removed under reduced pressure, affording 1-phenyl-1-(2-indanyl)-4-methyl-n-propyl-aminobutane.

I claim:

1. A method of treating cardiac arrhythmias comprising administering to a human subject suffering from an arrhythmia and in need of treatment a compound of the formula

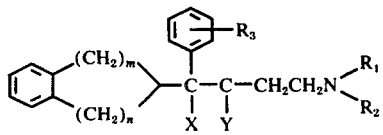

wherein:
 $m$ is 0, 1, or 2; $n$ is 0, 1, or 2; $m + n$ is 2 or 3;
 $R_1$ and $R_2$ independently are hydrogen, $C_1$-$C_4$ alkyl, lower alkenyl of the formula $CH_2R_4$, wherein $R_4$ is $C_2$-$C_5$ alkenyl,
 $R_3$ is hydrogen, methyl, methoxy, trifluoromethyl, or halogen;
 X and Y are both hydrogen, or taken together form a double bond; or
 the pharmaceutically acceptable acid addition salts thereof; in the amount of about 0.005 to about 2.0 g. at intervals of about 4 to about 10 hours, either orally or parenterally.

2. The method according to claim 1 wherein in the compound being administered, $R_1$ and $R_2$ independently are $C_1$-$C_4$ alkyl.

3. The method according to claim 2 wherein in the compound being administered, $m$ is 1 and $n$ is 1.

4. The method according to claim 3 wherein the compound administered is 4-phenyl-4-(2-indanyl)-1-diethylaminobutane

* * * * *